US012618103B2

(12) United States Patent
Yang et al.

(10) Patent No.: US 12,618,103 B2
(45) Date of Patent: May 5, 2026

(54) INSTRUMENT AND METHOD FOR EXTRACTING AND DETECTING NUCLEIC ACIDS

(71) Applicant: Jiaxing Accunome Biotechnology Co., Ltd., Jiaxing (CN)

(72) Inventors: Xing Yang, San Diego, CA (US); Xianhua Wang, Beijing (CN); Yang Song, Beijing (CN); Jianxin Ye, Beijing (CN); Wei Zhang, Beijing (CN)

(73) Assignee: Jiaxing Accunome Biotechnology Co., Ltd., Jiaxing (CN)

( * ) Notice: Subject to any disclaimer, the term of this patent is extended or adjusted under 35 U.S.C. 154(b) by 1024 days.

(21) Appl. No.: 17/641,518

(22) PCT Filed: Sep. 8, 2020

(86) PCT No.: PCT/CN2020/113968
§ 371 (c)(1),
(2) Date: Mar. 9, 2022

(87) PCT Pub. No.: WO2021/047499
PCT Pub. Date: Mar. 18, 2021

(65) Prior Publication Data
US 2022/0333180 A1     Oct. 20, 2022

(30) Foreign Application Priority Data

Sep. 10, 2019     (CN) .......................... 201910853057.9
Dec. 31, 2019     (CN) .......................... 201911403549.4

(51) Int. Cl.
C12Q 1/6851     (2018.01)
C12Q 1/6806     (2018.01)
(Continued)

(52) U.S. Cl.
CPC ....... *C12Q 1/6851* (2013.01); *G01N 21/6428* (2013.01); *G01N 35/0098* (2013.01);
(Continued)

(58) Field of Classification Search
None
See application file for complete search history.

(56) References Cited

U.S. PATENT DOCUMENTS 5,578,494 A * 11/1996 Clark ...................... B29C 45/00
220/283
6,309,603 B1 * 10/2001 Locke ...................... B67B 7/02
81/3.55
(Continued)

FOREIGN PATENT DOCUMENTS

CN        1974015 A       6/2007
CN      202830011 U       3/2013
(Continued)

OTHER PUBLICATIONS

CN 107893020 A (Machine translation) (Year: 2018).*
(Continued)

Primary Examiner — Samuel C Woolwine
(74) Attorney, Agent, or Firm — Fox Rothschild LLP

(57) ABSTRACT

Provided is a device for extracting and detecting nucleic acids, comprising one or more sample receiving modules, one or more lysing modules, one or more extraction module of nucleic acids, one or more amplification module of nucleic acids, and a detection module. Also provided is a molecular in vitro diagnostic instrument comprising the device for extracting and detecting nucleic acids and an automatic control system. Further provided is an in vitro diagnosis method by means of performing extraction and amplification of nucleic acids in a sample using the device for extracting and detecting nucleic acids.

21 Claims, 7 Drawing Sheets

(51) Int. Cl.

| | | |
|---|---|---|
| *G01N 21/64* | (2006.01) | |
| *G01N 35/00* | (2006.01) | |
| *G01N 35/10* | (2006.01) | |

(52) U.S. Cl.

CPC ..... *G01N 35/0099* (2013.01); *G01N 35/1011* (2013.01); *C12Q 1/6806* (2013.01); *G01N 2021/6432* (2013.01); *G01N 2035/00366* (2013.01); *G01N 2035/1053* (2013.01)

(56) References Cited

U.S. PATENT DOCUMENTS

| | | | |
|---|---|---|---|
| 10,401,373 | B1 | 9/2019 | Holmes et al. |
| 10,471,433 | B1 * | 11/2019 | Bell .......................... B01L 9/06 |
| 2007/0017927 | A1 * | 1/2007 | D'Amore ............ B01L 3/50825 |
| | | | 220/752 |
| 2009/0130745 | A1 | 5/2009 | Williams et al. |
| 2012/0255154 | A1 * | 10/2012 | Seitel ................... B65B 7/2842 |
| | | | 269/57 |
| 2012/0282603 | A1 | 11/2012 | Hansen et al. |
| 2015/0151300 | A1 | 6/2015 | Williams et al. |
| 2016/0376137 | A1 * | 12/2016 | Bell ........................ B67B 1/045 |
| | | | 53/381.4 |
| 2019/0391170 | A1 * | 12/2019 | Kochar .................. G06Q 10/10 |
| 2021/0291190 | A1 * | 9/2021 | Newman-Lehman ....................... |
| | | | G16B 25/00 |

FOREIGN PATENT DOCUMENTS

| | | | | | |
|---|---|---|---|---|---|
| CN | 103013814 | A | 4/2013 | | |
| CN | 106715673 | A | 5/2017 | | |
| CN | 107287092 | A | 10/2017 | | |
| CN | 107893020 | A | 4/2018 | | |
| CN | 108660074 | A | 10/2018 | | |
| CN | 108865659 | A | 11/2018 | | |
| CN | 212894763 | U | 4/2021 | | |
| WO | WO-2013019911 | A1 * | 2/2013 | ............... | B67B 7/02 |

OTHER PUBLICATIONS

CN 108660074 A (Machine translation) (Year: 2018).*

International Search Report issued on Mar. 18, 2021 for International Patent Application No. PCT/CN2020/113968 (5 pages).

Lu et al., Biotechnology and Principles for Pulp Bleaching (Second Edition), Jan. 2012, Papermaking Science and Technology Monograph Series.

English translation of First Office Action mailed on Nov. 19, 2024 in Chinese Patent Application No. 201911403549.4.

English translation of second Rejection Decision mailed on Sep. 20, 2025 in Chinese Patent Application No. 201911403549.4.

Zhaofang et al., Medical Laboratory Instrumentation, National-level Excellent Course "Twelfth Five-Year Plan" Textbook for Medical Laboratory Science Major in Higher Medical Colleges Nationwide, Huazhong University of Science and Technology Press, Jul. 2013, www.hustp.com.

* cited by examiner

INSTRUMENT AND METHOD FOR EXTRACTING AND DETECTING NUCLEIC ACIDS

This application is the U.S. national phase of International Patent Application No. PCT/CN2020/113968, filed on Sep. 8, 2020, which claims the priority of the following Chinese patent applications: the invention titled "instrument and method for extraction and detection of nucleic acids" with application No. 201910853057.9 filed on Sep. 10, 2019; and the invention titled "instrument and method for extraction and detection of nucleic acids" with application No. 201911403549.4 filed on Dec. 31, 2019", which are incorporated herein by reference in their entirety.

TECHNICAL FIELD

The present invention relates to the field of in vitro diagnostic devices. Specifically, the present invention provides an automated instrument for extraction and amplification of nucleic acids, and a method for detection and diagnosis using the instrument.

BACKGROUND OF ART

The extraction of biologically active substances (such as cells, proteins, nucleic acids and other biologically active substances) plays an important role in modern clinical disease diagnosis, blood transfusion safety, forensic identification, environmental microbial testing, food safety testing, molecular biology research and other fields. Among them, nucleic acids are biologically active substance compounds formed by the polymerization of many nucleotides, which is one of the most basic substances of life. Nucleic acids are widely found in all animals, plant cells, microorganisms, and living organisms. According to the chemical composition, nucleic acids can be divided into ribonucleic acid, referred to as RNA and deoxyribonucleic acid, referred to as DNA. DNA is the main material basis for storing, replicating and transmitting genetic information, and RNA plays an important role in the process of protein synthesis. With the rapid development of biotechnology, with the application of PCR technology in various fields, including medical disease detection, agricultural GMO detection and many other applications, methods and instruments for extracting nucleic acid from samples and detecting them are required.

However, at present, regardless of the methods, high-throughput fully automatic instruments have become the bottleneck in the application of PCR technology in the field of diagnostic analysis. There are several reasons for this. First, many diagnostic analyses are performed only with highly specialized equipment, which is expensive and can only be performed by trained clinicians. There is often only one such device in certain regions. This means that most hospitals need to send samples to these locations for analysis, thus incurring shipping costs and delays, and may even result in sample loss or incorrect functioning. Second, the equipment in question generally does not run as needed, but runs in batches after accumulating a certain amount, so there is a delay in processing for many samples, which creates a lot of uncertainty about the accuracy of the final result influence.

Therefore, there is a need for instruments and methods for extraction and analysis of nucleic acid that are as automated as possible, while being suitable for operation at any time, and better able to avoid contamination. For example, once extracted from a patient, the biological samples must be placed in a form suitable for PCR processing to amplify the target vector such as nucleotide. Once amplified, the target nucleotide from the sample needs to be clearly identified. Also, the instrument should have high throughput, especially for a single sample to perform multiple different analyses; and in a manner that can be routinely performed at the point of care, without the need to send the sample to specialized equipment for testing.

SUMMARY OF THE INVENTION

The device for extracting and detecting nucleic acids and the automated molecular in vitro diagnostic instrument provided by the present invention have high throughput, and can flexibly allocate throughput according to requirements, and can not only detect multiple samples at the same time, but also conduct a variety of different tests and analysis on one sample.

Specifically, the present invention provides a device for extracting and detecting nucleic acids, the device comprises:
  one or more sample receiving modules, each sample receiving module comprises a chamber adapted to receive a sample or sample container;
  one or more lysing modules, each lysing module comprises a chamber adapted to receive a lysing reagent or a lysing kit;
  one or more extraction module of nucleic acids, each extraction module of nucleic acids comprises a chamber adapted to receive nucleic acid extraction reagents or nucleic acid extraction kits;
  one or more amplification module of nucleic acids, each amplification module of nucleic acids comprises a plurality of chambers adapted to receive nucleic acid amplification reagents or nucleic acid amplification kits; and
  a detection module.

In one aspect of the present invention, the sample receiving module in the device has a sample holder for receiving sample tubes, which is arranged at the front end of the device close to the operator.

In one aspect of the present invention, the sample is lysed in the lysing module by means of a lysing reagent, an enzyme, ultrasound or physical grinding.

In one aspect of the present invention, the lysing modules further comprises an element for lysing sample.

In one aspect of the present invention, the element for lysing sample in the device is an oscillator composed of an eccentric shaft, an eccentric seat and a motor, an eccentric shaft rotates around the axis of the motor, causing the eccentric seat to oscillate.

In one aspect of the present invention, the lysing module in the device is adapted to receive grinding particles or a lysing kit comprising grinding particles to lyse the sample by means of physical grinding.

In one aspect of the present invention, the lysing kit comprises a lysing tube for receiving the grinding particles. In one aspect of the present invention, the lysing tube has a cap, and the inner wall has two or more axial protrusions.

In one aspect of the present invention, the lysing modules in the device is adapted to receive a lysing reagent or a lysing kit comprising a lysing reagent to chemically or biologically lyse a sample.

In one aspect of the present invention, the extraction module of nucleic acids in the device comprises one or more nucleic acid extraction units. In yet another aspect of the present invention, the nucleic acid extraction unit is composed of a binding unit, a washing unit, and an eluting unit.

In one aspect of the present invention, the extraction module of nucleic acids in the device comprises a magnet device that can apply a magnetic field to control a magnetic material and/or a nucleic acid-binding magnetic material.

In one aspect of the present invention, the device comprises a dispensing tube that can go into a binding unit, a washing unit and an eluting unit with properly designed mechanical movement, the nucleic acid in the container is extracted by the magnetic bead method, wherein after the nucleic acid sample is combined with the magnetic beads in the solution of the container, the tip of the dispensing tube is inserted into the bottom of the container, the magnet is close to the dispensing tube, and the magnetic beads and the bound sample are adsorbed to the side wall of the dispensing tube by the magnet, after the liquid is dispensed, the dispensing tube is moved to another container, the magnet leaves the dispensing tube, the effect of the magnetic field disappears, and the adsorbed magnetic beads and samples are released.

In one aspect of the present invention, the amplification module of nucleic acids in the device is configured for isothermal amplification or PCR, preferably, suitable for fluorescent quantitative PCR of DNA and RNA.

In one aspect of the present invention, the amplification module of nucleic acids in the device comprises a plurality of nucleic acid amplification units. Each nucleic acid amplification unit generally corresponds to a nucleic acid extraction sample obtained by each nucleic acid extraction unit in the extraction module of nucleic acids. The nucleic acid amplification unit corresponding to the nucleic acid extraction sample obtained by each nucleic acid extraction unit in the extraction modules of the nucleic acids comprises two or more chambers that independently perform amplification reactions. In one aspect of the present invention, each nucleic acid amplification unit may perform two or more identical or different amplification reactions on the same nucleic acid extraction sample.

In one aspect of the present invention, the amplification module of nucleic acids in the device further comprises a temperature regulator that can independently heat or cool each of the plurality of chambers. Each chamber can independently perform a different or the same amplification reaction.

In one aspect of the present invention, the amplification module of nucleic acids in the device further comprises a capping mechanism to close the cap of the amplification tube. In one aspect of the present invention, the capping mechanism comprises a cap assembly and a motion assembly, and the cap assembly comprises a cap clamping plate and a stepping motor, the stepping motor controls the up and down movement of the cap clamping plate; the motion assembly can move back and forth in the horizontal direction, and the amplification chamber of the amplification module of nucleic acids is connected to the motion assembly; the capping mechanism is configured so that when the amplification chamber or the amplification tube in the nucleic acid amplification kit moves with the motion assembly to be close to the cap clamping plate, the stepping motor drives the cap clamping plate to move up, slowly lift the cap of the amplification tube, and flip the tube cap; when the cap of the amplification tube is lifted to an appropriate angle, the cap clamping plate no longer moves upward, and the motion assembly continues to move toward the cap clamping plate, and then the stepping motor drives the clamping plate to move downward to press the tube cap tightly.

In one aspect of the present invention, the detection module detects identifiable labels carried by nucleic acids, including but not limited to fluorescence or other forms of luminescence (e.g. chemiluminescence, bioluminescence, radioluminescence, electroluminescence, electrochemiluminescence, mechanoluminescence, crystalline luminescence, thermoluminescence, sonoluminescence, phosphorescence and photoluminescence, etc.), enzymatic reactions, radioactivity, and the like.

In one aspect of the present invention, the detection module in the device comprises a fluorescence analyzer.

In one aspect of the present invention, the device further comprises a liquid dispensing module to transfer or dispense samples, reagents or other liquids in the device between two or more locations.

In one aspect of the present invention, the liquid dispensing module in the device comprises: one or more sensors; one or more dispensing heads; and a Cartesian coordinate robot that provides 3-axis linear movement for the dispensing heads.

In one aspect of the present invention, the device further comprises a reagent and consumable loading area.

In one aspect of the present invention, the reagent and consumable loading area in the device comprises one or more of a pipette tip loading area, a PCR reagent storing and mixing processing area, and a waste area.

The present invention also provides an automated molecular in vitro diagnostic instrument, comprising the above-mentioned device for extracting and detecting nucleic acids, and for example a computer-based automatic control system.

In one aspect of the present invention, the diagnostic instrument is used for infection source identification, genetic disease, cancer detection or gene mutation detection.

In one aspect of the present invention, the diagnostic instrument is used for detection of the following pathogens: influenza virus, enterovirus, hepatitis B virus, hepatitis C virus, Ebola virus, Marburg virus, SARS virus, Zika virus, Bunya virus, rhinovirus, respiratory nucleovirus, cholera virus and other viral pathogens, or *Mycobacterium tuberculosis, Escherichia coli, Acinetobacter baumannii, Streptococcus pneumoniae, Streptococcus lactis, Urea sporococcus, Aureus Staphylococcus aureus, Bacillus subtilis, Bacillus anthracia, Bacillus subtilis, Streptococcus, Proteus, Vibrio cholerae, Treponema pallidum* and other bacterial pathogens.

In one aspect of the present invention, the diagnostic instrument is used for detection of the following cancers: gastric cancer, liver cancer, lung cancer, esophageal cancer, cervical cancer, breast cancer, colon cancer, rectal cancer, nasopharyngeal cancer, ovarian cancer, kidney cancer, bladder cancer, thyroid cancer and skin cancer, etc.; malignant tumors that grow from mesenchymal tissues such as muscle, fat, bone, blood vessels, lymph, etc., for example, rhabdomyosarcoma, leiomyosarcoma, fibrosarcoma, liposarcoma, osteosarcoma, chondrosarcoma, angiosarcoma, lymphosarcoma, etc., also e.g. leukemia, Hodgkin's disease, Wilm's tumor (Wilms tumor), melanoma, retinocytoma, seminoma, granulosa cell tumor, Krukenberg tumor, Ewing's tumor, malignant hemangioendothelioma, or Paget's disease of the breast.

The present invention also provides an in vitro diagnosis method, wherein the above-mentioned device for extracting and detecting nucleic acids or the above-mentioned diagnostic instrument is used to perform nucleic acid extraction and amplification on the sample.

In one aspect of the present invention, the method is used for infection source identification, genetic disease, cancer detection, or genetic mutation detection.

In one aspect of the present invention, the method is used for detection of the following pathogens: influenza virus, enterovirus, hepatitis B virus, hepatitis C virus, Ebola virus, Marburg virus, SARS virus, Zika virus, Bunya virus, rhinovirus, respiratory nucleovirus, cholera virus and other viral pathogens, or *Mycobacterium tuberculosis, Escherichia coli, Acinetobacter baumannii, Streptococcus pneumoniae, Streptococcus lactis, Urea sporococcus, Aureus Staphylococcus aureus, Bacillus subtilis, Bacillus anthracia, Bacillus subtilis, Streptococcus, Proteus, Vibrio cholerae, Treponema pallidum* and other bacterial pathogens.

In one aspect of the present invention, the method is used for detection of the following cancers: gastric cancer, liver cancer, lung cancer, esophageal cancer, cervical cancer, breast cancer, colon cancer, rectal cancer, nasopharyngeal cancer, ovarian cancer, kidney cancer, bladder cancer, thyroid cancer and skin cancer, etc.; malignant tumors that grow from mesenchymal tissues such as muscle, fat, bone, blood vessels, lymph, etc., for example, rhabdomyosarcoma, leiomyosarcoma, fibrosarcoma, liposarcoma, osteosarcoma, chondrosarcoma, angiosarcoma, lymphosarcoma, etc. Also, e.g. leukemia, Hodgkin's disease, Wilm's tumor (Wilms tumor), melanoma, retinocytoma, seminoma, granulosa cell tumor, Krukenberg tumor, Ewing's tumor, malignant hemangioendothelioma, or Paget's disease of the breast.

DESCRIPTION OF THE DRAWINGS

Other features, objects and advantages of the present invention will become more apparent upon reading the detailed description of non-limiting embodiments with reference to the following drawings.

BEST MODES OF CARRYING OUT THE PRESENT INVENTION

Figure 1:
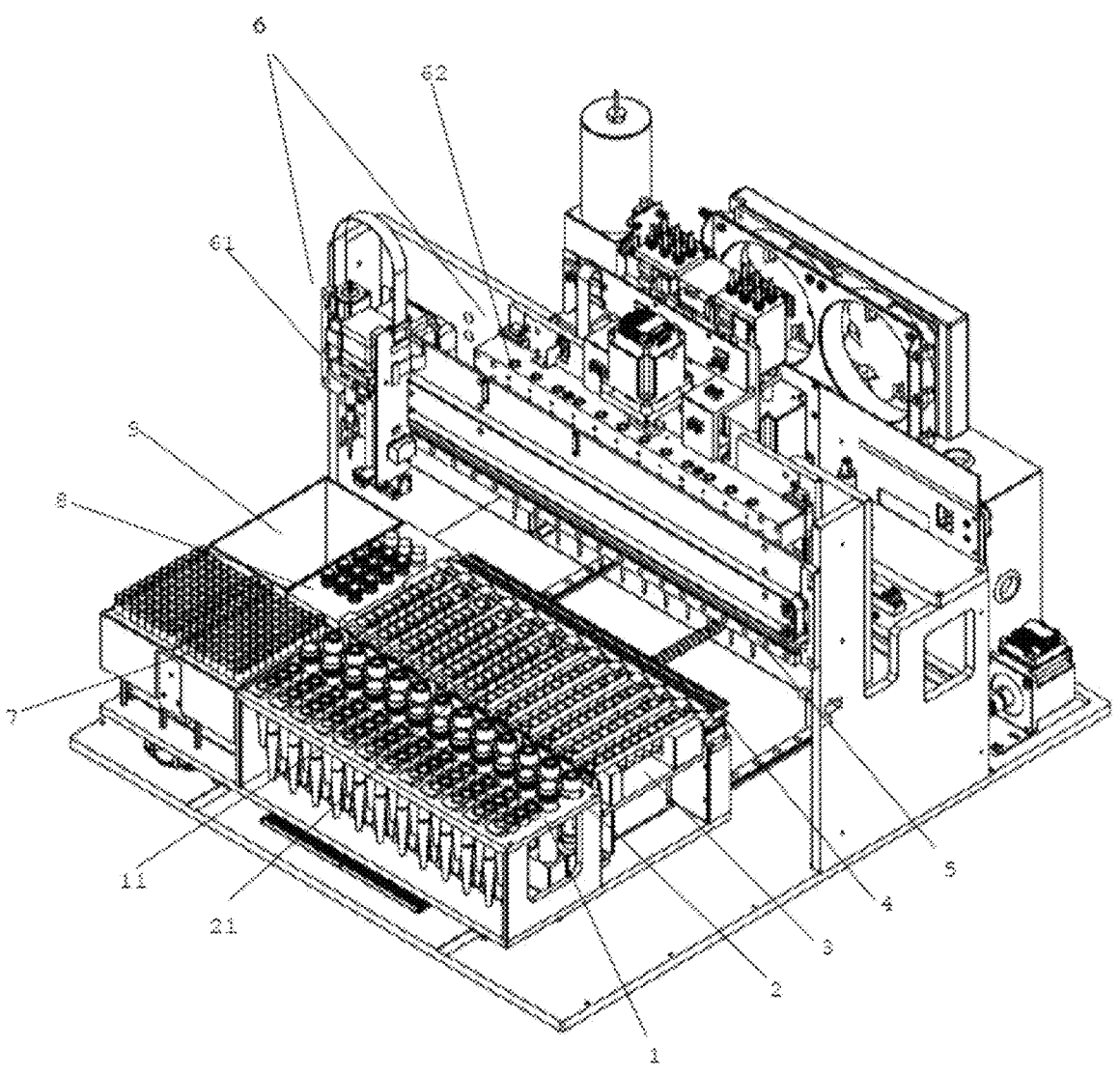
FIG. 1 is a perspective view of an exemplary device of the present invention.

The term nucleic acid as used herein includes DNA (deoxyribonucleic acid) and RNA (ribonucleic acid). It is also understood that the terms nucleic acid and polynucleotide may be used interchangeably herein.

It should be understood that the devices described herein should be used to analyze any nucleic acid-containing sample for any purpose, including but not limited to genetic testing of human genes and clinical testing of various infectious diseases. Nucleic acid samples used in the methods described herein may be from any source. Typically, a sample may be a biological material that is separated from its natural environment and contains polynucleotides. A sample may consist of purified or isolated polynucleotides, or may comprise a biological sample such as a tissue sample, biological fluid sample, or a cell sample comprising the polynucleotides. Biological fluids include, by way of non-limiting examples, blood, plasma, sputum, urine, cerebrospinal fluid, lavage samples. Nucleic acid samples may be originated from plant, animal, bacterial or viral sources. Samples may be obtained from different sources, including but not limited to samples from different individuals, different developmental stages of the same or different individuals, different diseased individuals (e.g., individuals with cancer or suspected of having a genetic disorder), normal individuals, the same or different individuals in different stages of diseases, individuals undergoing different treatments of diseases, individuals exposed to different environmental factors, or individuals with susceptible constitutions, or individuals exposed to infectious disease reagents such as HIV.

As used herein, the term "unit" is used to denote an element or combination of elements configured to operate together to implement one or more functions or produce one or more desired results, wherein each element may individually have, clear and/or independent functions. It is to be understood that each element within the unit need not be directly connected or in direct communication with each other elements. Also, the connection or communication of the various elements may be accomplished with the aid of elements external to the unit, such as a processor.

As used herein, the term "module" is used to denote a unit or combination of units configured to operate together to implement one or more subsystem functions of the device of the present invention. It is to be understood that each unit within the module need not be directly connected or in direct communication with each other units. Also, the connection or communication of the various units may be accomplished with the aid of units or elements external to the module, such as a processor.

The "magnetic material" referred to in this specification includes various materials having magnetic properties, including particles and particulate materials having various particle size distributions. The shape of the material is not limited to spherical materials, any shape is allowed.

The present invention provides a device for separating or obtaining nucleic acids from a sample and detecting it by polymerase chain reaction.

In order to better understand and explain the present invention, the present invention will be further described in detail below with reference to the accompanying drawings.

Figure 2:
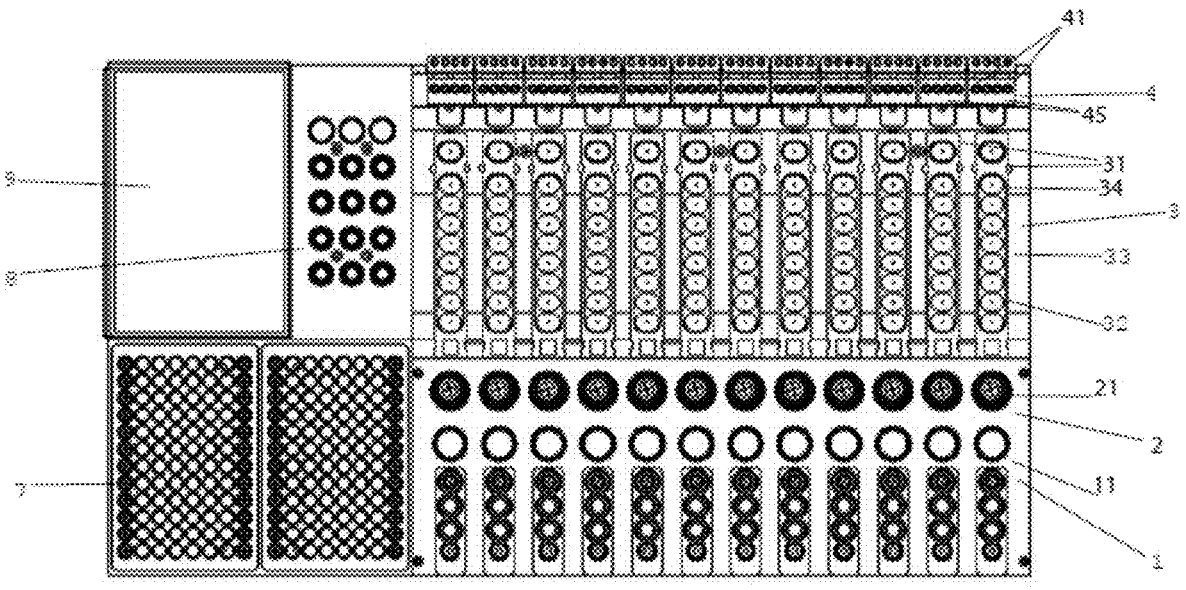
FIG. 2 is a schematic diagram of a partial plane layout of an exemplary device of the present invention.

See FIGS. 1 and 2. FIG. 1 is a perspective view of an exemplary device of the present invention, and FIG. 2 is a schematic diagram of a partial plane layout of an exemplary device of the present invention.

As shown in FIG. 1, the device of the present invention comprises:

one or more sample receiving module 1, comprising a chamber adapted to receive a sample or sample container;

one or more lysing module 2, comprising a chamber adapted to receive a lysing kit; in the lysing module of FIG. 1, there are also elements for lysing the sample;

one or more extraction module of nucleic acids 3, each extraction module of nucleic acids comprises a chamber adapted to receive nucleic acid extraction kits, comprising a binding unit, a washing unit, an eluting unit, and a magnet device movable relative to each binding, washing or elution unit;

one or more amplification module of nucleic acids 4, each amplification module of nucleic acids comprises two or more chamber is adapted to receive nucleic acid amplification kits;

a detection module 5; and a liquid dispensing module 6 for transferring or dispensing samples, reagents or other liquids in the device between two or more locations.

Sample Receiving Module

Figure 3:
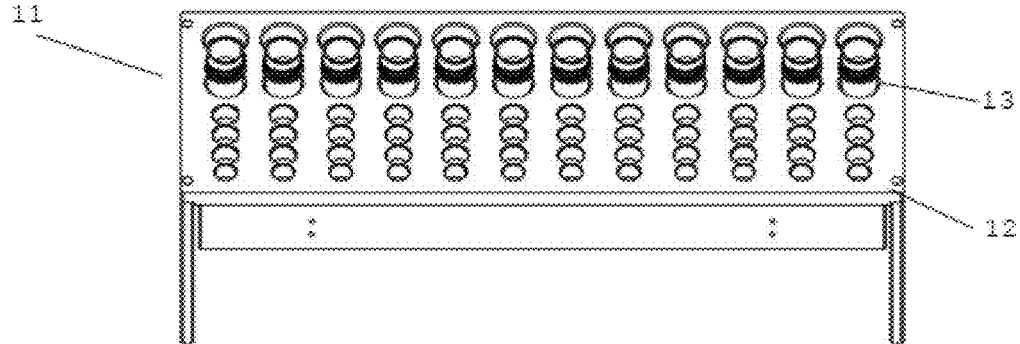
FIG. 3 is a structural diagram of an exemplary sample holder of the device of the present invention.

In the present invention, the device of the present invention has a sample receiving module 1 having a chamber adapted to receive a sample or sample container. In one embodiment of the present invention, the chamber adapted to receive the sample container is the sample holder 11. An exemplary sample holder may be as shown in FIG. 3, which includes a rack 12 and a sample tube well 13 into which sample tubes are inserted.

An example of a sample container is a sample tube. The sample tube may be a standard sample tube, such as a standard blood collection tube or a BD sample tube. The sample tube suitable for the device of the present invention may be any commercially available sample tube, such as but not limited to 12/13×75 mm glass tube for blood collection, 12/13×75 mm plastic tube for blood collection, 13×100 mm blood collection tube, 16×75 mm blood collection tube, 16×100 mm blood collection tube, 16×100 mm BD sample tube, etc. The sample tube may also be a non-standard sample tube. The type of sample tube selected depends on the consumables and the design of a sample tube rack. In the instrument and method of the present invention, for a sample that does not require additional diluent, the minimum sample volume of the sample tube may be as high as 500 µl. For samples that require the use of diluent (or a small sample volume), the minimum sample volume for the sample tube may be 100 µl or less. In the example as shown in FIG. 3, a row of one sample holder can receive 12 sample tubes. The sample holder may be arranged at the front end of the experimental area close to the operator in the device of the present invention, so as to facilitate the operation.

In an embodiment of the present invention, the sample holder or sample tube is further attached with a barcode. The barcode may be scanned externally (e.g., using a hand-held laboratory (clinical laboratory) information system), built-in scanner, or an automatic scanning device built into the instrument, thereby recording and monitoring the samples to be tested.

Lysing Modules

The device of the present invention is used for obtaining nucleic acid of a sample and a method for its detection. The device of the present invention comprises a lysing module 2 for lysing the sample cells so that the nucleic acids coated by the cell membrane are released.

As shown in FIGS. 1 and 2, the lysing module 2 of the device of the present invention comprises a chamber adapted to receive a lysing reagent or a lysing kit. The lysing module of the device of the present invention may lyse the sample by means of lysing reagents, enzymes, ultrasound or physical grinding. It is necessary to add lysing reagents (including various reagents and/or solutions for lysing sample cells) to lyse cells. Lysing reagents are also available as lysing kits (e.g., lysing reagent tubes) that contain lysing reagents.

In one embodiment of the present invention, the lysing module lyses the samples by means of lysing reagents. The lysing reagents that can be used in the present invention include various surfactants such as SDS, Triton X, NP-40, etc., as well as other chemical reagents such as buffers, protease inhibitors, reducing reagents, etc., the main functions thereof is: (1) to destroy lipid bilayers and rupture cells by using detergent; (2) to dissolve proteins; (3) to promote protein denaturation; (4) to inhibit the activity of proteases and nucleases. In this embodiment of the invention, the element used to lyse the sample is an element that facilitates sample lysis by the lysing reagents, including, but not limited to, an optional heating element, an oscillation generator that facilitates mixing of the mixture of lysing reagents and samples, or a dispensing tube that could aspirate and dispense mixture repeatedly, etc. The lysing reagent is included in the lysing kit of the present invention, and may be in the lysing tube, or in other containers of the lysing kit, and may or may not be connected to the lysing tube.

In one embodiment of the present invention, the lysing module lyses the samples by means of enzymatic lysing. The enzymes that can be used in the present invention may be various enzymes that lyse components of the cell wall or cell membrane, for example, Labiase lyase, lysostaphinase, egg protein-derived lysozyme, human-derived lysozyme, achromopeptidase, *Streptomyces coccidioides* derived mutanolysin, *Staphylococcus aureus* derived α-hemolysin, chitinase, *Rhizoctonia solani*-derived lyase, *Arthrobacter luteus*-derived lyase, *Trichoderma harzianum*-derived lyase, *Streptococcus pyogenes*-derived streptolysin O, Tetanus tetanus hemolysin, etc. In this embodiment of the invention, the element used to lyse the sample is an element that facilitates enzymatic lysing of the sample, including, but not limited to, an optional heating element, an oscillation generator that facilitates mixing of the mixture of enzymes and samples, or a dispensing tube that is repeatedly aspirated, etc. The enzymes may be included in the lysing kit of the present invention, and may be in the lysing tube, or in other containers of the lysing kit, and may or may not be connected to the lysing tube.

In one embodiment of the present invention, the lysing module lyses the sample by means of ultrasound. Ultrasonic lysis involves the use of ultrasonic heating to disrupt cells. However, this treatment is prone to DNA fragmentation, so the time and gap time for ultrasonic lysis should be set to avoid damaging the target DNA. In this embodiment of the invention, the element used to lyse the sample is, for example, a sonicator, and optionally a heating or cooling element that maintains the temperature of the sample. Optionally, the sample is sonicated after mixing with a diluent or buffer. The diluent or buffer may be included in the lysing kit of the present invention, in the lysing tube, or in other containers of the lysing kit, and may or may not be connected to the lysing tube.

In one embodiment of the present invention, the lysing module lyses the samples by means of physical grinding. Physical grinding refers to the mechanical crushing of fine particles with a certain hardness, that is, grinding particles, such as glass beads or ceramic beads, by vortex oscillation with the sample. It makes use of the rapid movement of grinding particles to impact the sample cells to mechanically disrupt to lyse the sample cells. Compared with other methods, physical grinding is a powerful lysing method with higher lysing efficiency, more uniform and comprehensive lysing of cells, and higher DNA yield.

Figure 4:
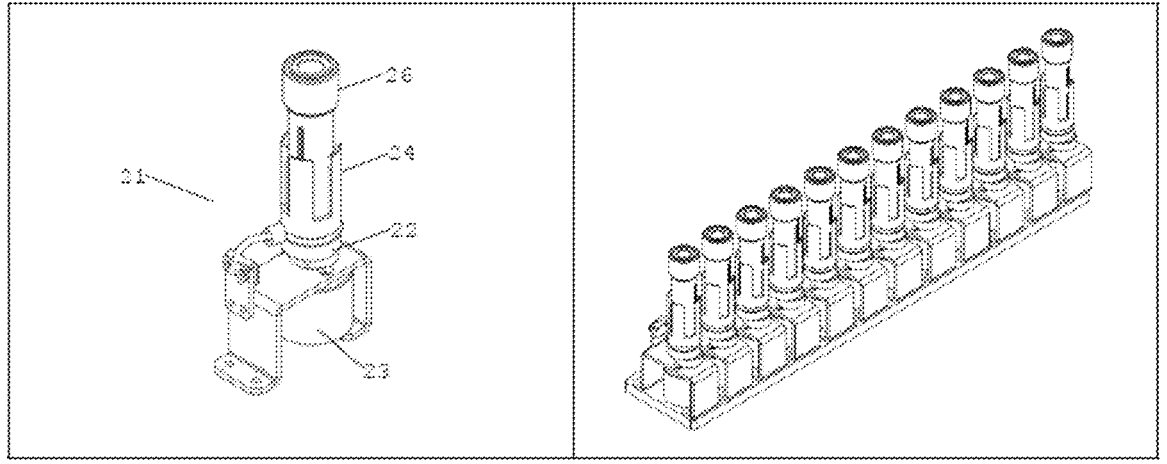
FIG. 4 is a structural diagram of an exemplary lysing module of the device of the present invention.

In the lysing module of the exemplary device of the present invention, as shown in FIG. 4, there is a chamber adapted to receive a sample tube or lysing kit for the lysing reagents, and elements for lysing the sample by means of physical grinding. In this embodiment of the invention, the element used to lyse the sample is the oscillator 21. As shown in FIG. 4 on the left, the oscillator 21 uses the eccentric shaft 22 to rotate around the axis of the DC motor 23, so that the eccentric seat 24 vibrates at a high speed. The sample container is placed in the eccentric seat, and the glass beads or ceramic beads added to the sample vibrate at high speed to achieve the purpose of disrupting the cells in the sample. The exemplary lysing module as shown in FIG. 4 on the right has 12 oscillators that can process 12 samples simultaneously, and to drive 12 eccentric seats through 12 independent motors, so that the sample tube containing the lysing reagents or the samples in the lysing kit placed in the eccentric seat rotates and collides with the glass beads or ceramic beads therein at high speed. The motor and its rotational speed as used in the device of the present invention can be determined by those skilled in the art according to the prior art or limited experiments.

In the above exemplary device of the present invention, a lysing kit may be used in the lysing module. In the above-mentioned embodiment of the present invention in which the sample is lysed by means of physical grinding, the lysing kit has a fixed or detachable lysing tube containing the samples/lysing reagents.

Also included in the lysing kit are grinding particles, such as glass beads or ceramic beads for grinding, having a particle size of about 0.1-1 mm. The grinding particles may be placed in the lysing tube, or in other containers of the lysing kit that may or may not be connected to the lysing tube. The lysing kit has a sealing film on the surface that encloses the grinding particles or lysing reagents within the lysing kit. During work, the operator tears off the sealing film on the surface of the lysing kit, and then places the lysing kit in the corresponding chamber of the lysing module of the device of the present invention.

Figure 5:
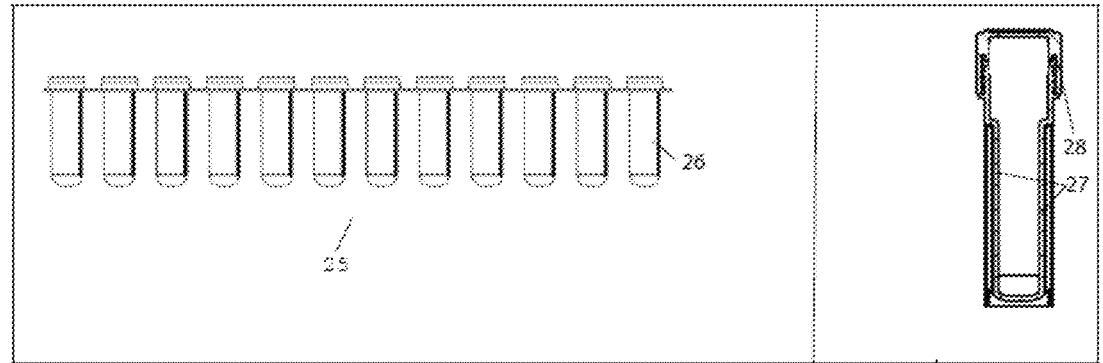
FIG. 5 is an exemplary lysing kit of the present invention.

In the exemplary lysing kit 25 as shown in FIG. 5, it comprises 12 lysing tubes 26, where each lysing kit can be used for the lysis of one sample, as shown in FIG. 5 on the left. FIG. 5 on the right is a cross-sectional view of the lysing tube 26, which shows that the lysing tube 26 has a cap 28, and its inner wall has at least two symmetrical axial protrusions 27.

In one embodiment of the present invention, the sample added to the device of the present invention does not require additional addition of diluent. In this case, the minimum loading volume may be 50 µl, or 100 µl, or may be as high as 500 µl.

Extraction Module of Nucleic Acids

The device of the present invention is used for obtaining nucleic acid of a sample and a method for its detection. The device of the present invention comprises an extraction module of nucleic acids 3, which is used for separating and obtaining nucleic acid in a sample. In one embodiment of the invention, after sample lysis, a liquid dispensing module transfers the lysed sample from the lysing module, e.g., the above-mentioned lysing kit, to the extraction module of nucleic acids.

As shown in FIGS. 1 and 2, the extraction module of nucleic acids 3 of the device of the present invention comprises a chamber adapted to receive the nucleic acid extraction reagents or nucleic acid extraction kits. The extraction module of nucleic acids of the device of the present invention extracts nucleic acid through the steps of binding, washing and eluting of nucleic acids, wherein binding reagents, washing reagents and eluting reagents of nucleic acids (including magnetic beads for extracting nucleic acids, washing solution, eluting solution, etc.) need to be added. Binding reagents, washing reagents and eluting reagents of nucleic acids may also be provided in the form of nucleic acid-binding kits (e.g., nucleic acid-binding reagent tubes) containing the reagents.

In the method and device of the present invention, the extraction of nucleic acid is performed by the magnetic bead method. The nucleic acid is bound by contacting a magnetic material and/or a binding solution that can bind to nucleic acids with the sample that has been subjected to the lysis step, thereby binding the nucleic acid to the magnetic material. The complex formed after the nucleic acid is combined with the magnetic material can be controllably moved, stirred or precipitated in the container under the action of a magnetic field, so as to achieve the purpose of binding, washing and eluting of nucleic acids.

As shown in the schematic diagram of a partial plane layout of the exemplary device of FIG. 2, in one embodiment of the present invention, the extraction module of nucleic acids of the device of the present invention has 12 nucleic acid extraction units 31, and each nucleic acid extraction unit is composed of a binding unit 32, a washing unit 33, and an eluting unit 34, as shown in FIG. 2. Each nucleic acid extraction unit is used to process one sample to obtain one nucleic acid extraction sample. The binding unit 32 of the extraction module of nucleic acid is a hole that accommodates a magnetic material and/or a binding solution that can bind to nucleic acids, or is suitable for receiving a corresponding binding tube in the nucleic acid extraction kit, and the binding tube contains a magnetic material and binding solution that can bind to nucleic acids. When a nucleic acid extraction kit is used, after the nucleic acid extraction kit is put into the device of the present invention, a liquid dispensing module is added to the binding tube. The washing unit 33 is a plurality of holes that accommodate the washing solution or is suitable for receiving corresponding washing tubes in the nucleic acid extraction kit. When a nucleic acid extraction kit is used, after the nucleic acid extraction kit is put into the device of the present invention, the liquid dispensing module is added to the washing tube. The eluting unit 34 is a hole that accommodates the eluting solution, suitable for receiving the corresponding eluting tube in the nucleic acid extraction kit.

The extraction module of nucleic acids includes a magnet for moving magnetic material and nucleic acid bound to the magnetic material between the binding units, washing units or eluting units by a magnetic field.

Figures 6, 7:
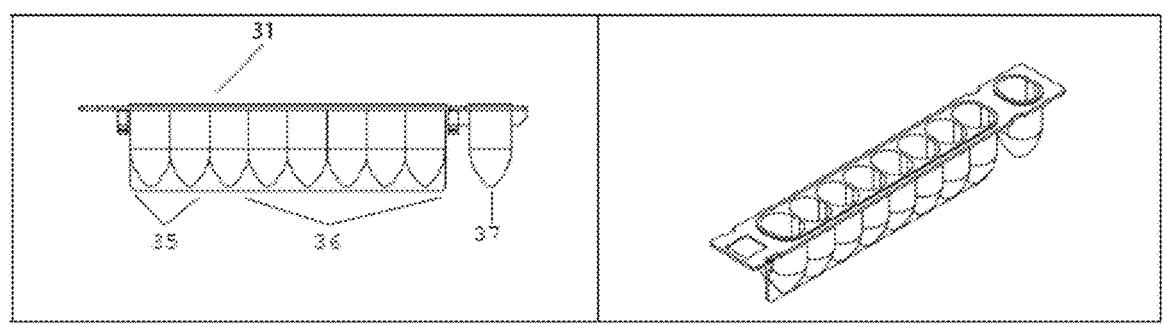
FIG. 6 is a schematic diagram of an exemplary extraction module of nucleic acids using the magnetic bead method of the present invention, and a method for controlling adsorption and pipetting in the module by a magnetic field.
FIG. 7 is a structural diagram of an exemplary nucleic acid extraction kit of the present invention.

FIG. 6 is a schematic diagram of an exemplary extraction module of nucleic acids using a magnetic bead method, and a method for controlling adsorption and pipetting by a magnetic field in the module. In the system and method for magnetic field-controlled adsorption and pipetting of the exemplary magnetic bead method as shown in FIG. 6, the lysed sample is bound to the magnetic beads by the binding tube 35, the pipette tip of the dispensing tube 39 is inserted into the bottom of the magnetic bead binding tube, the magnet 38 is close to the dispensing tube, and during the slow upward aspirating process, the magnetic beads are adsorbed to the side wall of the dispensing tube by the magnet. After pipetting all the sample liquid up, the dispensing tube and the magnet move upward synchronously, and then the liquid is dispensed. After the adsorption action of the side wall is completed, the horizontal movement of the mechanical arm moves the dispensing tube to the washing tube 36, the magnet leaves the dispensing tube, the magnetic field disappears, the adsorbed magnetic beads and samples are released, the pipette tip of the dispensing tube is inserted under the liquid surface, and the magnetic beads enter the washing tube through repeated up and down aspirating and dispensing. Similarly, the magnetic material in the washing tube may be transferred to the eluting tube 37 by the same method, and the magnetic material may be brought into the eluting solution in the eluting tube. After the elution is completed, by applying a magnetic field, the magnetic material that is no longer bound to the nucleic acid is adsorbed to the side wall of the dispensing tube, so that the magnetic material is separated from the eluting solution.

Similarly, the magnetic material in a washing tube may be transferred to another washing tube in a similar manner, or to an eluting tube. In one embodiment of the present invention, each extraction module of nucleic acids includes a plurality of washing units, such as 2-5, preferably 3. Correspondingly, each nucleic acid extraction kit includes a plurality of washing tubes, such as 2-5, preferably 3.

In one embodiment of the invention, a magnet device is provided to be movable to the side of the dispensing tube. In one embodiment of the present invention, the magnet device, such as electromagnet, is provided to be fixed to the dispensing tube of the liquid dispensing module, a magnetic field is applied to the dispensing tube by periodically energizing and de-energizing. In one embodiment of the invention, the magnet device, e.g., permanent magnet or electromagnet, is provided to be movable relative to the dispensing tube, e.g., closer to or away from the dispensing tube, to periodically apply a magnetic field to the dispensing tube. The magnet device may be moved with the dispensing tube relative to the binding, washing or eluting unit, e.g., closer or further away, to transfer the magnetic material from one unit to another. In this way, the magnet device periodically applies a magnetic field to the dispensing tube from which the magnetic material accumulates in the liquid dispensing module (e.g., the dispensing tube) when the magnetic field is applied, and transfers from the liquid dispensing module (e.g., the dispensing tube) to other modules when the magnetic field is removed.

In one embodiment of the invention, after sample lysis, the liquid dispensing module transfers the lysed sample from the lysing kit to the nucleic acid extraction kit located in the extraction module of nucleic acids. For example, the liquid dispensing module draws the lysed sample into the dispensing tube, then the Cartesian coordinate robot unit moves the dispensing head and dispensing tube to the nucleic acid extraction kit, and finally dispenses the lysed sample into the nucleic acid extraction kit, such as in the binding tube suitable for the binding unit.

According to the present invention, the lysed sample is drawn into the dispensing tube by the liquid dispensing module, moved with the dispensing tube and then dispensed into the binding unit in the extraction module of nucleic acids, e.g., in the binding tube of a nucleic acid extraction kit located in the binding unit. The lysed sample is bound to the magnetic material in the binding tube. After a period of binding, the tip of the dispensing tube is inserted into the bottom of the binding tube. Then, the magnet device applies a magnetic field to the dispensing tube, so that the magnetic material bound with nucleic acid is adsorbed to the side wall of the dispensing tube by the magnetic field during the slow upward aspirating process of the dispensing tube. After aspirating all the liquid up, the dispensing tube moves upwards synchronously with the magnet device, and then dispenses the liquid without magnetic material out of the dispensing tube. After the adsorption action of the side wall is completed, the liquid dispensing module moves the dispensing tube horizontally to the washing tube located in the washing unit, and then the magnet device removes the magnetic field applied to the dispensing tube, so that the magnetic material is released. When the tip of the dispensing pipe is inserted under the liquid surface, the liquid dispensing unit drives the liquid in the dispensing tube to repeatedly enter and exit the dispensing tube, so that the magnetic material enters the washing liquid in the washing tube.

Finally, the liquid dispensing module moves the magnetic material-adsorbed dispensing tube away from the eluting unit, leaving only the nucleic acid-containing eluting solution in the eluting tube. Dispensing tubes with adsorbed magnetic material can be released from the liquid dispensing module to the waste area.

Preferably, the binding unit, the washing unit and the eluting unit respectively comprise heating elements to heat the reaction reagents (e.g., binding or eluting solution) and the magnetic material to promote the binding or separation of the nucleic acid and the magnetic material.

In the above-mentioned exemplary device of the present invention, a nucleic acid extraction kit can be used in the extraction module of nucleic acids. The nucleic acid extraction kit includes a binding tube, one or more washing tubes, and an eluting tube, and each contains a magnetic material, a washing solution, an eluting solution, etc. that can bind to nucleic acid. In the exemplary nucleic acid extraction kit 31 as shown in FIG. 7, it can be a single-channel reagent tube. FIG. 7 on the left is a front view of the nucleic acid extraction kit, and FIG. 7 on the right is a perspective view. The nucleic acid extraction kit of the present invention can also be multi-packed, for example, 12 packs, wherein each nucleic acid extraction kit can perform nucleic acid extraction from one lysed sample.

The binding tube 35, the washing tube 36 and the eluting tube 37 in the nucleic acid extraction kit have sealing film. The sealing film can adopt a double-film structure, in which the inner film is a rubber or silicone film with a cross-like shape, and the sealing film is an aluminum-plastic or plastic sealing film to prevent the liquid from splashing during the transportation of reagents. When pipetting, the dispensing tube is pipetted through the cross. A barcode can be attached to the kit, and the barcode contains information such as the expiration date of the reagents.

Amplification Module of Nucleic Acids

The device of the present invention is used for a method for amplifying and detecting nucleic acids in a sample. The device of the present invention comprises an extraction module of nucleic acid 4 for amplifying nucleic acids in the sample. In one embodiment of the present invention, after nucleic acid extraction, the liquid dispensing module transfers the sample from the extraction module of nucleic acids, e.g., the above-mentioned nucleic acid extraction kit, to the amplification module of nucleic acids.

In one embodiment of the invention, the amplification module of nucleic acids is a module suitable for nucleic acid amplification in any manner, including but not limited to various isothermal amplification or PCR, such as qPCR (fluorescent quantitative PCR), RT-PCR, hot-start PCR, nested PCR, multiplex PCR, reconditioning PCR, dsRNA synthesis, COLD-PCR, digital PCR, etc. Preferably, the amplification module of nucleic acid is configured for fluorescence quantitative PCR of DNA and RNA.

As shown in FIGS. 1 and 2, the amplification module of nucleic acids 4 of the device of the present invention has a plurality of chambers 41 adapted to receive nucleic acid amplification reagents or nucleic acid amplification kits. Each of the chambers can perform an independent amplification reaction. In one embodiment of the present invention, in the amplification module of nucleic acids, the nucleic acid amplification unit corresponding to the nucleic acid extraction sample obtained by each nucleic acid extraction unit in the extraction module of nucleic acids comprises a nucleic acid amplification unit that performs two or more amplification reactions. The chamber, i.e., each nucleic acid amplification unit, can perform two or more identical or different amplification reactions on the same nucleic acid extraction sample. In one embodiment of the present invention, each nucleic acid amplification unit corresponding to the nucleic acid extraction sample obtained by each nucleic acid extraction unit in the extraction module of nucleic acids has 2-30 chambers, preferably 3-10 chambers, most preferably 4-8 chambers.

As shown in the schematic diagram of a partial plane layout of an exemplary device of FIG. 2, in one embodiment of the present invention, the device of the present invention has 12 nucleic acid extraction units 31, each nucleic acid extraction unit corresponds to an amplification unit 45 (i.e., the exemplary device has 12 amplification units 45), the amplification unit has 4 amplification chambers 41, each of which can perform an independent amplification reaction. The templates for amplification reactions performed in several amplification chambers in one amplification unit are all derived from the extracted samples provided by the same nucleic acid extraction unit; the amplification reactions of the several amplification chambers in each amplification unit are independent, e.g., the same or different PCR primer pairs may be used, or different PCR reaction conditions, e.g., temperature, may be used.

In the above exemplary device of the present invention, a nucleic acid amplification kit can be used in the amplification module of nucleic acids, which includes two or more amplification tubes, and a premixed reagent containing all the components required for the nucleic acid amplification reaction. The premixed reagent can be placed in the amplification tube, or can be transferred to the amplification tube by the liquid dispensing module in a separate container that may or may not be connected to the amplification tube. Preferably, each nucleic acid amplification kit preferably includes 2-30 amplification tubes, preferably 3-10, and most preferably 4-8.

Figure 8:
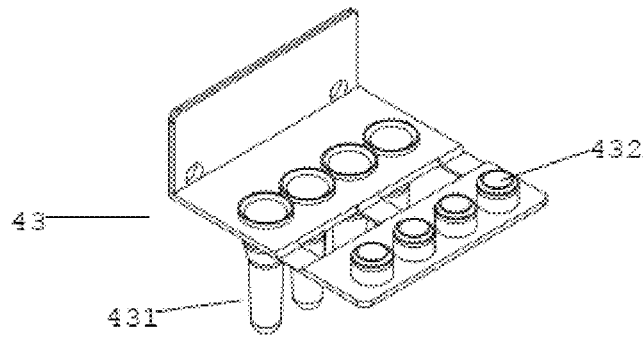
FIG. 8 is an exemplary flip system of the device of the present invention.

The exemplary nucleic acid amplification kit 43 as shown in FIG. 8 is in quadruple form, including 4 amplification tubes 431. The amplification tubes are reaction cups with caps 432, the bottom end of the cup body is a conical structure, and the upper end is cylindrical. The effective volume of the amplification tube is usually about 1-100 μl, preferably about 10-50 μl, more preferably about 30 μl.

The inventors of the present invention have found that the challenge with using PCR as a primary method of diagnosis is the presence of various possible pathogenic microorganisms and low levels of microorganisms in certain samples. It is often impractical to run large numbers of PCRs, and in some cases there may not be enough samples to assay for all possible pathogens. The present invention, by creatively including two or more chambers adapted to receive nucleic acid amplification kits in each amplification module of nucleic acids, and using nucleic acid amplification kits comprising two or more amplification tubes enables multiplex PCR analysis to be performed on one sample at the same time to detect multiple targets. This not only reduces sample volume requirements, but also increases system throughput in a similar configuration, thereby reducing the cost of assays.

In one embodiment of the present invention, the amplification module of nucleic acids further comprises a temperature regulator that can independently heat or cool each of the plurality of chambers 41, so that each chamber can independently perform different or the same amplification reactions. In one embodiment of the invention, the amplification module of nucleic acids operates at a constant temperature, and a temperature regulator keeps the various chambers of the device of the invention at a constant temperature. In another embodiment of the present invention, the temperature regulator cyclically heats and cools the various chambers of the device of the present invention in a predetermined program for a predetermined period of time. The temperature, duration, and number of cycles of heating and cooling can be determined by those skilled in the art from prior art or limited experimentation, and all such embodiments are included within the scope of the present invention.

In the PCR reaction, the amplification reaction of the sample must be carried out in a closed environment. Nucleic acid amplification chambers or amplification tubes in nucleic acid amplification kits have caps that can be opened or closed. In one embodiment of the present invention, the amplification module of nucleic acids further includes a flip system to tightly close the cap of the amplification tube in the nucleic acid amplification kit of the amplification module of nucleic acids to prevent evaporation of liquid and generation of air bubbles during amplification, which affects the accuracy of the response.

Figure 9:
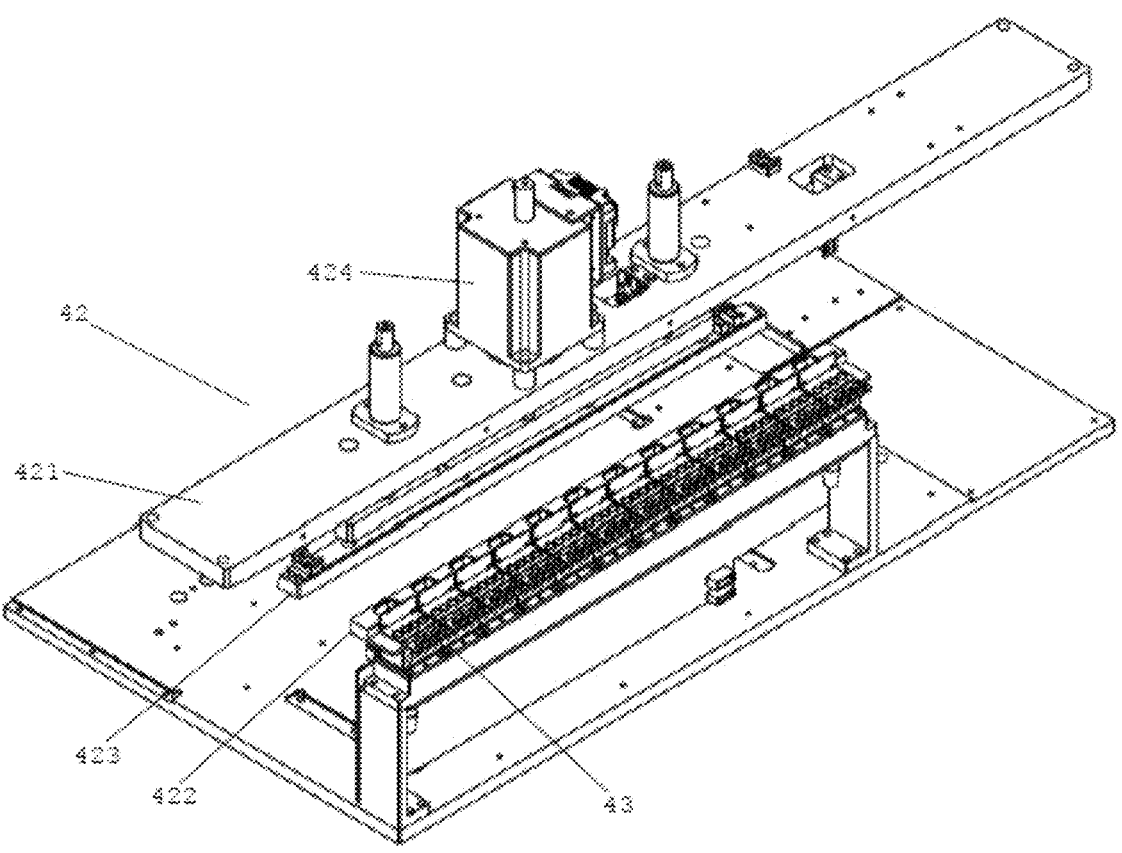
FIG. 9 is a structural diagram of an exemplary nucleic acid amplification kit of the present invention.

In the exemplary flip system 42 as shown in FIG. 9, the flip system has a cap assembly 421 and a motion assembly 422. The cap assembly 421 includes a cap clamping plate 423 and a stepping motor 424, and the stepping motor controls the cap clamping plate to move up and down. The motion assembly can move back and forth in the horizontal direction, and the amplification chamber of the amplification module of nucleic acids is connected with the motion assembly. When the amplification chamber or the amplification tube in the nucleic acid amplification kit moves with the motion assembly 422 to approach the cap clamping plate 423, the stepping motor 424 drives the cap clamping plate 423 to move upward, and during the upward movement, the cap clamping plate 423 is moved upward. The cap of the amplification tube is lifted slowly, and the tube cap is flipped to realize the function of flipping the cap. When the cap of the amplification tube is lifted to an appropriate angle, the cap clamping plate 423 will no longer move upward, and the motion assembly 422 will continue to move in the direction of the cap clamping plate 423. When the amplification tube moves to just below the cap clamping plate 423, the tube cap is also located above the tube mouth, and then the stepping motor 424 drives the cap clamping plate 423 to move downwards, and presses the tube cap tightly to realize the capping function.

According to the present invention, the liquid dispensing module picks up the dispensing tube, enables fluid connection with the dispensing head, and then moves to the top of the eluting unit to aspirate the eluting solution, then moves to the amplification tube and dispenses the eluting solution into one or more amplification tubes. Alternatively, the liquid dispensing module returns to the eluting unit after dispensing the eluting solution, and aspirates the eluting solution again and transfers the eluting solution to another one or more amplification tubes, and the cycle is repeated one or more times. In one embodiment of the present invention, the MIX reagent is placed in the reagent position, and the reagent position is kept at 4-8° C. during the operation of the instrument. After the eluting solution is transferred into the amplification tube, the liquid dispensing module transfers the MIX reagent into the amplification tube with the eluting solution, and repeatedly aspirates and dispenses to mix the reagent system. The liquid dispensing module can then be moved to the waste area, and the dispensing tube is removed so that a new dispensing tube is used each time the MIX reagent is pipetted into the amplification tube.

Finally, the temperature regulator independently heats or cools each amplification tube according to a predetermined program, and performs a certain number of thermal cycles to amplify the target nucleic acid. For efficiency, heat and cool as quickly as possible each time. In one embodiment of the invention, each temperature regulator also has an associated temperature sensor.

A Detection Module

The device of the present invention is used for a method for amplifying and detecting nucleic acid of a sample. The device of the present invention comprises a detection module 5 used for detecting the amplified nucleic acid.

The detection module of the present invention is a module suitable for detecting identifiable labels carried by nucleic acids in any manner, including but not limited to fluorescence or other forms of luminescence (e.g. chemiluminescence, bioluminescence, radioluminescence, electroluminescence, electrochemiluminescence, mechanoluminescence, crystalline luminescence, thermoluminescence, sonoluminescence, phosphorescence and photoluminescence, etc.), enzymatic reactions, radioactivity, and the like. In one aspect of the invention, detection of amplified nucleic acid is achieved by detection of a fluorescent signal carried by the nucleic acid.

As shown in FIGS. 1 and 2, the device of the present invention comprises a detection module 5. In one embodiment of the present invention, the detection module is a fluorescence analyzer for excitation and detection of fluorescence, which is arranged to be fixed or movable to the side of the amplification module of nucleic acids, for example, to the side of the amplification tube, and the amplification tube is scanned linearly laterally.

Figure 10:
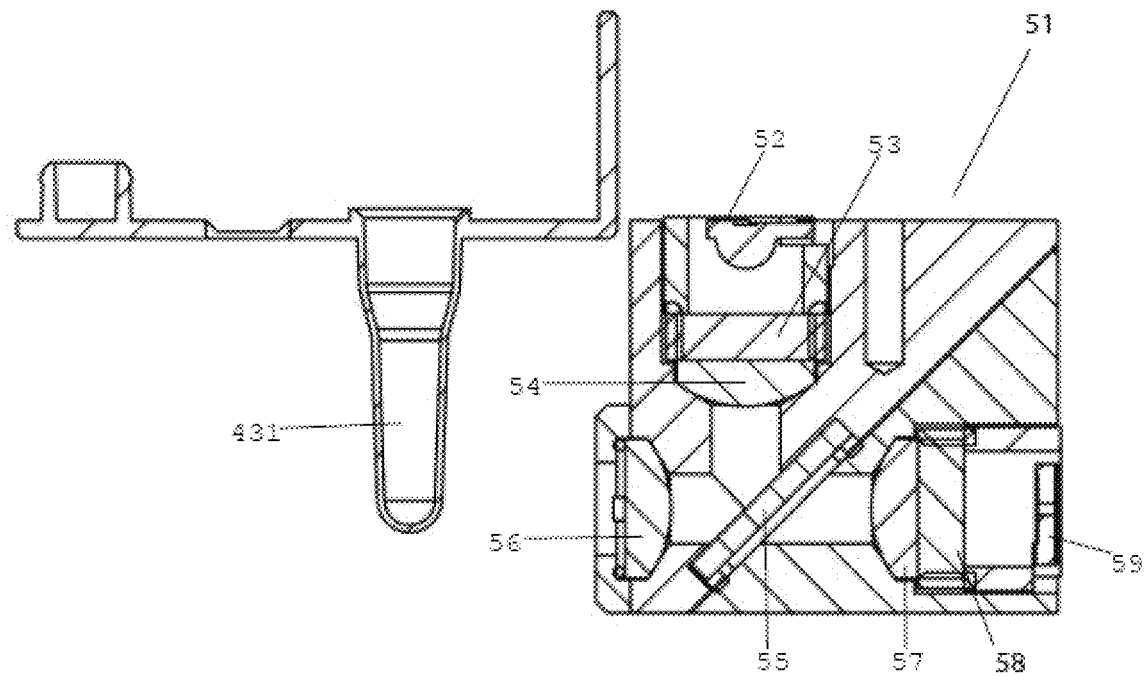
FIG. 10 is a schematic diagram of the structure and light path of an exemplary fluorescence analyzer of the device of the present invention.

In the schematic diagram of the structure and light path of the exemplary fluorescence analyzer 51 as shown in FIG. 10, each light path is composed of the excitation light source 52, the excitation light filter 53, the first convex lens 54, the dichroic mirror 55, the second convex lens 56, the third convex lens 57, the emission light filter 58 and the detector 59. As shown in FIG. 10, the excitation light source 52 is an LED, and the emitted light is transformed into parallel light through the excitation light filter 53 and the first convex lens 54, and the parallel light is reflected to the second convex lens 56 through the dichroic mirror 55, and converges and irradiates the PCR reaction tube, for example, the amplification tube 431, which excites the sample to emit fluorescence; the excited fluorescence is transformed into parallel light through the second convex lens 56, the parallel light passes through the dichroic mirror 55, passes through the third convex lens 57 and the emission filter 58 and converges on the detector 59, and the detector converts it into a fluorescence signal. The fluorescence analyzer in the device of the present invention can detect various kinds of fluorescence, including FAM, ROX, CY5, VIC and so on. The light path of the fluorescence analyzer may be one light path, or may be multiple light paths corresponding to each amplification tube.

The LED light excites the fluorescent molecules (initially attached to the nucleic acid probes) in the amplification tube, causing them to fluoresce. In the beginning, this fluorescence will typically be effectively blocked by closely spaced quencher molecules. DNA amplification occurs upon DNA amplification via the TAQ enzyme if the target sequence (DNA sequence) of the probe is present in the sample chamber, after annealing, the nucleic acid probe binds to the amplified target sequence, so that the fluorescent molecule and the quenching molecule are separated, and the fluorescence cannot be quenched. Fluorescence occurs when a fluorescent molecule is illuminated by excitation light of a certain wavelength. The emitted light is different from the excitation light. Blue incident light is blocked from leaving the detector by the green separate emission filter. Green incident light is similarly blocked from leaving the detector by the yellow emission filter. Fluorescence is captured and propagates through a path into the focusing lens, through the filter and onto the sensitive photodiode.

A Liquid Dispensing Module

The device of the present invention is used for a method for extracting, amplifying and detecting nucleic acid of a sample, which comprises sample receiving modules, one or more lysing modules, one or more extraction module of nucleic acids, one or more amplification module of nucleic acids, and a detection module, each module also has its own operating unit in which liquid samples are transferred between modules and units.

As shown in FIGS. 1 and 2, in one embodiment of the present invention, the device of the present invention comprises a liquid dispensing module 6 for achieving the transfer of sample and solution.

In one embodiment of the present invention, the liquid dispensing module comprises one or more sensors; one or more dispensing heads; and a Cartesian coordinate robot that provides 3-axis linear movement for the dispensing heads. In one embodiment of the present invention, the sensor may, for example, be an infrared sensor for detecting the presence of a dispensing tube in a liquid dispensing module. For example, an infrared sensor may have an infrared emitter positioned relative to it, and the presence or absence of the dispensing tube obstructs the line of sight between the emitter and the sensor, whereby the presence or absence of the dispensing tube may be determined.

In one embodiment of the present invention, the sensors in the device of the present invention further comprises any sensors that controls the degree of horizontal or vertical movement of the dispensing head during its pick-up of the dispensing tube and fluid dispensing operation. For example, in one embodiment of the present invention, the sensor is a force sensor for controlling the degree of vertical movement of the dispensing head during its pick-up of the dispensing tube and fluid dispensing operation. The dispensing head can be mounted such that a force acting upwardly against the dispensing head can be sensed by relative motion between the dispensing head and the force sensor. For example, when the dispensing head exerts force against the dispensing tube below it, the transmitted upward force causes a squeeze against the force sensor. The force sensor then communicates with a processor or controller that controls vertical movement of the liquid dispensing module so that when an appropriate signal is received from the force sensor, the processor or controller can send instructions to prevent vertical movement of the liquid dispenser. Alternatively, in another embodiment of the present invention, as an alternative to force sensors, potentiometric sensors, magnetic position sensors, resolver sensors, proximity sensors, etc. may be used, all of which are included within the scope of the present invention.

In one embodiment of the present invention, a liquid dispensing module comprises one or more dispensing heads, each configured to receive a dispensing tube. The dispensing head may also comprises a ring movable relative to the dispensing head, configured to remove a dispensing tube fluidly connected to the dispensing head when moved to the end of the dispensing head. Multiple dispensing heads can be connected in parallel and fluidly connected to the same pump simultaneously, so that multiple dispensing tubes can be connected to the multiple dispensing heads to aspirate the same amount of liquid, allowing multiple parallel assays to be performed simultaneously. The dispensing head may also comprise a number of valves, such as solenoid valves configured to control the flow of air through the dispensing head.

In one embodiment of the present invention, the liquid dispensing module comprises a pump that is in fluid connection with one or more dispensing heads and is controllable by an associated controller in the device of the present invention. Various pumps suitable for the purpose of the present invention may be used in the device of the present invention, including but not limited to piston pumps, plunger pumps, diaphragm pumps, gear pumps, slide pumps, screw pumps, and the like.

Figure 11:
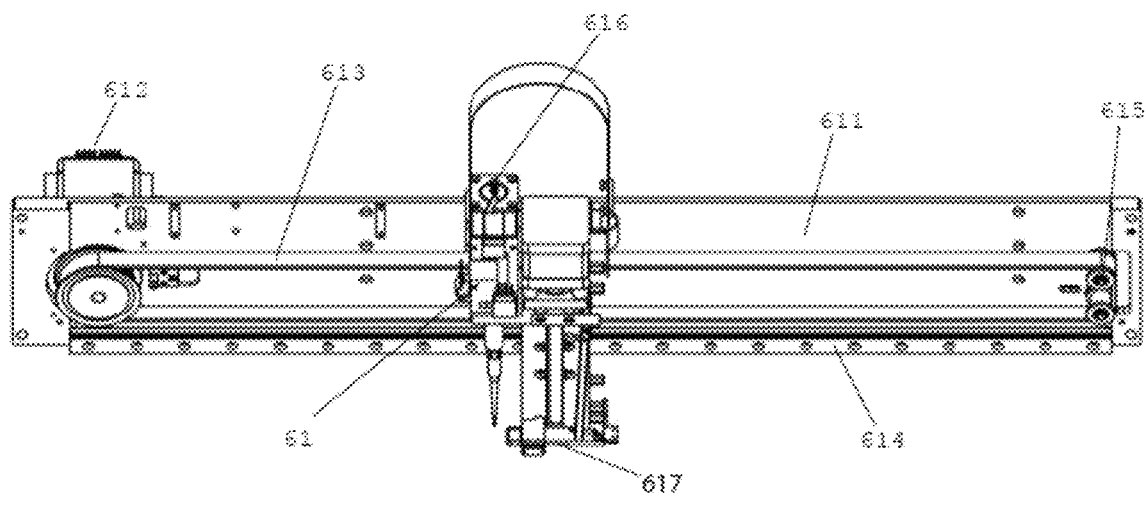
FIG. 11 is a schematic structural diagram of an exemplary liquid dispensing module of the device of the present invention.

FIG. 11 is a schematic structural diagram of an exemplary liquid dispensing modules of the device of the present invention. The liquid dispensing module is a single-arm pipette system for transferring sample diluents, loading of PCR samples and PCR reagent, etc. The single-arm pipette system has a single-arm pipette 61 and a Cartesian coordinate robot, which comprises a single-arm beam 611, a horizontal motion stepping motor 612, a synchronous belt 613, a wired guide rail 614, an idler 615, and a vertical motion stepping motor 616. The single-arm pipette system may also have a drip catching plate 617.

The single-arm pipette 61 is fixedly connected with the synchronous belt 613, and the horizontal movement of the single-arm pipette 61 is realized by controlling the horizontal motion stepping motor 612, the synchronous belt 613, and the idler 615. On the other hand, the single-arm pipette 61 is driven to move up and down by controlling the vertical motion stepping motor 616 and the slider assembly connector.

Figure 12:
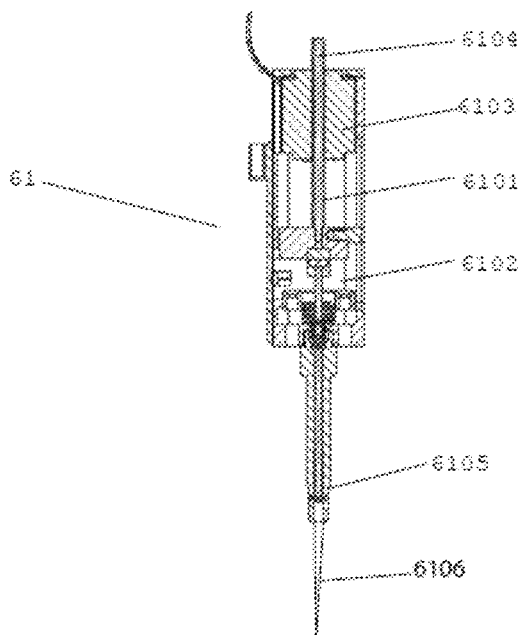
FIG. 12 shows a cross-sectional view of an exemplary single-arm pipette of the device of the present invention.

FIG. 12 shows a cross-sectional view of the single-arm pipette 61 of the device of a single-arm pipette system, the single-arm pipette 61 performs the operation of aspirating and dispensing the solution on the pipette tip 6106 detachably located at the bottom of the single-arm pipette through the piston structure. The piston structure comprises a piston rod 6101, a piston jacket 6102, a stepping motor 6103, and a stepping motor linear actuator 6104. The stepping motor 6103 drives the piston rod to move up and down through the stepping motor linear actuator 6104, so as to realize the functions of aspirating and dispensing liquid from the pipette tip. The single-arm pipette also has a tip ejection device 6105.

When the single-arm pipette 61 is connected to the pipette tip, the stepping motor 6103 of the single-arm pipette 61 drives the piston rod to move up and down through the stepping motor linear actuator 6104, so as to realize the functions of aspirating and dispensing liquid from the pipette tip. When the pipette tip moves downward to aspirate liquid, the drip catching plate moves to the underside of the pipette tip, and when the pipette tip moves upward, the drip catching plate moves to the bottom of the pipette tip to catch any liquid drip, so as to avoid the liquid dripping on the outer wall of the pipette tip and causing pollution.

The process of withdrawing the pipette tip is that when the stepping motor 6103 controls the movement to a certain position below, the tip ejection device 6105 connected to the top is pushed to remove the pipette tip.

Figure 13:
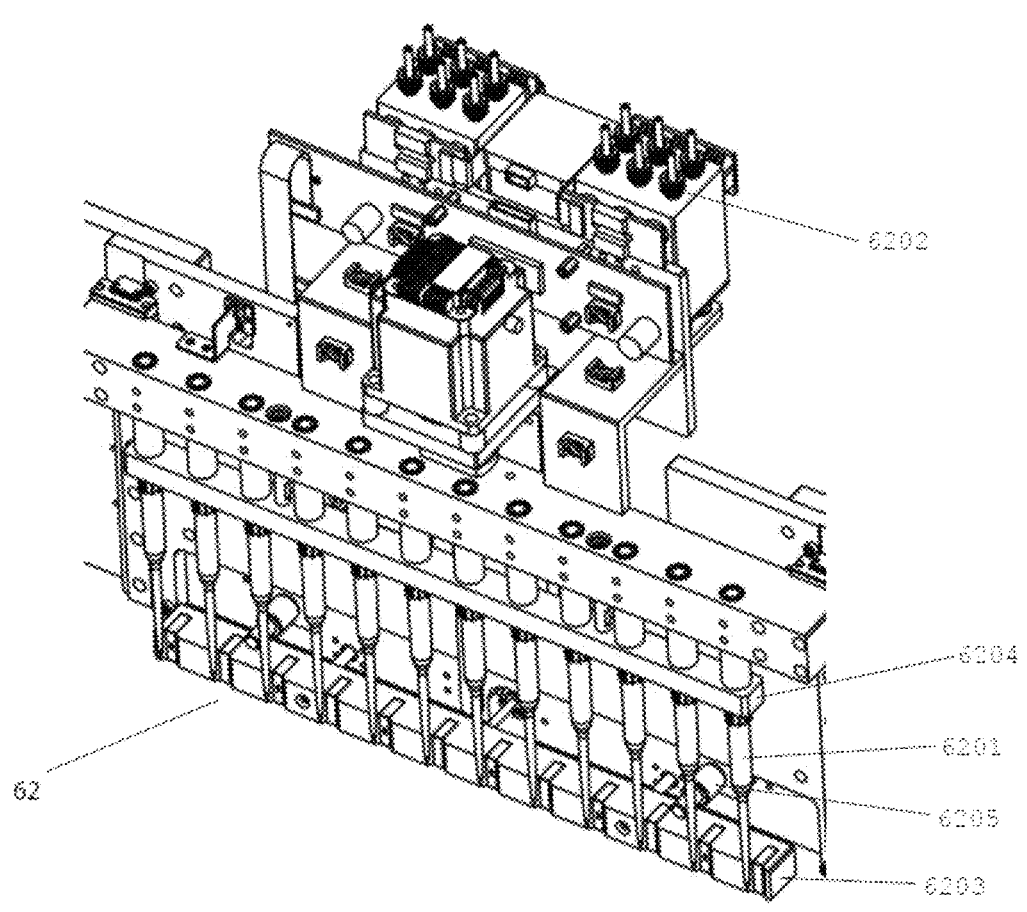
FIG. 13 is a schematic structural diagram of another exemplary liquid dispensing module of the device of the present invention.

FIG. 13 is a schematic structural diagram of another exemplary liquid dispensing module of the device of the present invention. The liquid dispensing module is a multi-channel pipetting system, which is used for sample pipetting, nucleic acid extraction, and PCR sample loading, and the nucleic acid extraction process is completed by the side wall adsorption of the magnet. The multi-channel pipetting system includes a multi-channel pipetting assembly and a Cartesian coordinate robot. The multi-channel pipetting assembly 62 comprises a plurality of pipettes 6201 arranged in parallel, a plurality of pumps 6202 and a magnet assembly 6203 in one-to-one correspondence with the plurality of pipettes connected by hoses. The multi-channel pipetting system realizes the transfer of liquid through plunger pumps. A plurality of pumps are respectively connected with the corresponding pipettes through hoses, and the plunger of the pump assembly moves up and down to complete the liquid aspirating and dispensing. The multi-channel pipetting system completes the side wall adsorption and release of magnetic particles and nucleic acids bound thereon through magnets.

The multi-channel pipetting assembly 62 may also have a tip ejection system, which comprises a stepping motor 6206 for controlling the up and down movement of the multi-channel pipettes, a pipette tip ejection plate 6204 and a bayonet lock 6205. The bayonet 6205 is pushed by the electromagnet and can be pushed forward, so that it is stuck on the top of the pipette tip ejection plate 6204. The stepping motor 6206 makes the multi-channel pipettes move upward, and the pipette tip ejection plate cannot move upward under the blocking of the bayonet lock, and the process of ejecting the pipette tip is completed.

The position movement of the multi-channel pipetting assembly 62 is realized by the movement of the Y-axis and the Z-axis.

In one embodiment of the present invention, a Cartesian coordinate robot of the multi-channel pipetting assembly 62 is a deck, for example, a deck with two-axis or three-axis linear movement, driven by a driving slide driven by a coded stepping motor.

When the dispensing head to be controlled is an independent single dispensing head (such as a single-arm pipette), it can be installed on a deck with three-axis linear movement, X (horizontal), Y (front and rear), and Z (up and down), such that it can be moved within the device of the invention to a unit of another module or in a kit located in that unit, for example a dilution tube of a dilution unit, an amplification tube in a chamber of a amplification module of nucleic acids, or a container containing MIX reagents. When a plurality of dispensing heads are connected in parallel, they can cover the entire horizontal range that they need to reach in the device of the present invention, so they can be installed on a deck with two-axis linear movement, Y (front and rear) and Z (up and down), and no horizontal movement is required within the device of the present invention. dispensing heads connected in parallel pick up one or more dispensing tubes at the same time and move to the desired position, for example, sample tubes, lysing tubes, eluting tubes, etc., aspirate the liquid in one or more tubes and transfer it to the desired position. In one embodiment of the present invention, a deck with two-axis linear movement and a deck with three-axis linear movement may coexist, which together constitute the Cartesian coordinate robotic unit of the present invention.

In one embodiment of the invention, the sensors and the dispensing heads are mounted on the Cartesian coordinate robotic unit. The pump may also be mounted on the Cartesian coordinate robotic unit, or in other parts of the device of the present invention, fluidly connected to the dispensing heads by means of tubing. Mounting can be by mechanical fastening, such as one or more screws.

A Reagent and Consumable Loading Area

The device of the present invention is used for a method for extracting, amplifying and detecting nucleic acid of a sample, which comprises the use of various reagents and consumables. As shown in FIGS. 1 and 2, in one embodiment of the present invention, the device of the present invention comprises a reagent and consumable loading area, such as a pipette tip loading area 7, a PCR reagent storing and mixing processing area 8, a waste area 9 etc.

In one embodiment of the invention, the device of the invention comprises a pipette tip loading area. The pipette tip loading area may be in any form provided that it is convenient to accommodate and replace the pipette tips used during the operation of the device of the present invention.

In one embodiment of the invention, the device of the invention comprises a PCR reagent storing and mixing processing area. PCR reactions require the use of reagents such as enzymes, reaction buffers, and water. These reagents can be stored separately in advance, or they can be mixed in advance according to the required ratio. The PCR reagent storing and mixing processing area may also have a temperature control system to cool and keep the relevant reagents warm.

In one embodiment of the present invention, the device of the present invention comprises a waste area. The waste area may be in any form so long as it can accommodate waste generated during operation of the device of the present invention. For example, the waste area may be a bucket or bag with an opening that can hold liquid.

An Automated Molecular In Vitro Diagnostic Instrument

The invention also provides an automated molecular in vitro diagnostic instrument. In one embodiment of the present invention, the molecular in vitro diagnostic instrument comprises the above-mentioned nucleic acid extraction and detection device, and a computer-based automatic control system.

The automatic system can control the liquid dispensing module of the nucleic acid extraction and detection device to programmatically transfer the sample between or within the sample receiving module, the lysing module, the extraction module of nucleic acids and the amplification module of nucleic acids of the above-mentioned device for extracting and detecting nucleic acids, and under suitable conditions, procedures such as lysing, extraction, amplification and inspection are performed according to predetermined steps, and the sample to be tested is detected. The diagnostic instrument can be used for infection source identification, genetic disease, cancer detection or gene mutation detection.

In one embodiment of the present invention, the diagnostic instrument can be used for the detection of the following pathogens: influenza virus, enterovirus, hepatitis B virus, hepatitis C virus, Ebola virus, Marburg virus, SARS virus, Zika virus, Bunya virus, rhinovirus, respiratory nucleovirus, cholera virus and other viral pathogens, or *Mycobacterium tuberculosis, Escherichia coli, Acinetobacter baumannii, Streptococcus pneumoniae, Streptococcus lactis, Urea sporococcus, Aureus Staphylococcus aureus, Bacillus subtilis, Bacillus anthracis, Bacillus subtilis, Streptococcus, Proteus, Vibrio cholerae, Treponema pallidum* and other bacterial pathogens.

In one embodiment of the present invention, the diagnostic apparatus can be used for the detection of the following cancers: gastric cancer, liver cancer, lung cancer, esophageal cancer, cervical cancer, breast cancer, colon cancer, rectal cancer, nasopharyngeal cancer, ovarian cancer, kidney cancer, bladder cancer, thyroid cancer and skin cancer, etc.; malignant tumors that grow from mesenchymal tissues such as muscle, fat, bone, blood vessels, lymph, etc., for example, rhabdomyosarcoma, leiomyosarcoma, fibrosarcoma, liposarcoma, osteosarcoma, chondrosarcoma, angiosarcoma, lymphosarcoma, etc. Also, e.g. leukemia, Hodgkin's disease, Wilm's tumor (Wilms tumor), melanoma, retinocytoma, seminoma, granulosa cell tumor, Krukenberg tumor, Ewing's tumor, malignant hemangioendothelioma, or Paget's disease of the breast. Analysis and diagnosis.

Although the exemplary embodiments of the present invention and their advantages have been described in detail, it should be understood that various changes, substitutions and alterations can be made hereto without departing from the spirit of the invention and the scope of protection defined by the appended claims. For other examples, those of ordinary skill in the art will readily understand that the order of the process steps may be varied while remaining within the scope of the present invention.

The invention claimed is:

1. A device for extracting and detecting nucleic acids, comprising:

one or more sample receiving modules, each sample receiving module comprises a chamber adapted to receive a sample or sample container;

one or more lysing modules, each lysing module comprises a chamber adapted to receive a lysing reagent or a lysing kit;

one or more nucleic acid extraction modules, each nucleic acid extraction module of nucleic acids comprises a chamber adapted to receive nucleic acid extraction reagents or a nucleic acid extraction kit;

one or more nucleic acid amplification modules, each nucleic acid amplification module comprises a plurality of chambers adapted to receive nucleic acid amplification reagents or an amplification tube of a nucleic acid amplification kit, wherein the one or more nucleic acid amplification modules further comprise a capping mechanism to close a cap of the amplification chamber or amplification tube, the capping mechanism comprising a cap assembly and a motion assembly, wherein the cap assembly comprises a cap clamping plate and a stepping motor, wherein the stepping motor controls up and down movements of the cap clamping plate, wherein the motion assembly is configured to move back and forth in the horizontal direction, wherein the amplification chamber of the nucleic acid amplification module is connected to the motion assembly, wherein the capping mechanism is configured so that:

when the amplification chamber or the amplification tube moves with the motion assembly to be close to the cap clamping plate, the stepping motor drives the cap clamping plate to move up, lifts the cap of the amplification chamber or the amplification tube, and flips the cap; and when the cap is lifted to an appropriate angle, the cap clamping plate no longer moves upward, the motion assembly continues to move toward the cap clamping plate, and then the stepping motor drives the clamping plate to move downward to press the cap;

wherein the device further comprises a detection module.

2. The device of claim 1, wherein the lysing module is configured to lyse the sample by means of a lysing reagent, an enzyme, ultrasound or physical grinding.

3. The device of claim 1, wherein the lysing module further comprises an oscillator composed of an eccentric shaft, an eccentric seat, and a motor, wherein the eccentric shaft rotates around an axis of the motor, causing the eccentric seat to oscillate.

4. The device of claim 3, wherein the lysing module is adapted to receive grinding particles or a lysing kit comprising grinding particles to physically grind the sample.

5. The device of claim 4, wherein the lysing kit comprises a lysing tube for receiving the grinding particles.

6. The device of claim 1, wherein the nucleic acid extraction module comprises one or more nucleic acid extraction units, wherein each of the one or more nucleic acid extraction units is composed of a binding unit, a washing unit, and an eluting unit.

7. The device of claim 6, further comprising a dispensing tube that is configured to go into a binding unit, a washing unit, and an eluting unit of the nucleic acid extraction module, wherein the nucleic acid extraction module is configured to:

combine the sample with magnetic beads in a solution in a container, whereby nucleic acids in the sample are bound by the magnetic beads;

insert the tip of the dispensing tube into the bottom of the container;

draw the solution containing the magnetic beads into the dispensing tube, whereby a magnet close to the dispensing tube adsorbs the magnetic beads to a side wall of the dispensing tube;

dispense the solution from the dispensing tube;

move the dispensing tube to another container; and move the magnet relative to the dispensing tube such that the effect of the magnetic field disappears and the magnetic beads are released from the side wall of the dispensing tube.

8. The device of claim 6, wherein the nucleic acid amplification module of comprises a plurality of nucleic acid amplification units, wherein each of the nucleic acid amplification units corresponds to a nucleic acid extraction sample obtained by a nucleic acid extraction unit in the nucleic acid extraction module, wherein each nucleic acid amplification unit comprises two or more chambers that are configured to independently perform amplification reactions.

9. The device of claim 1, wherein the nucleic acid extraction module comprises a magnet that is configured to apply a magnetic field to control a magnetic material and/or a nucleic acid-binding magnetic material.

10. The device of claim 9, further comprising a dispensing tube that is configured to go into a binding unit, a washing unit, and an eluting unit of the nucleic acid extraction module, wherein the nucleic acid extraction module is configured to:

combine the sample with magnetic beads in a solution in a container, whereby nucleic acids in the sample are bound by the magnetic beads;

insert the tip of the dispensing tube into the bottom of the container;

draw the solution containing the magnetic beads into the dispensing tube, whereby the magnet close to the dispensing tube absorbs the magnetic beads to a side wall of the dispensing tube, dispense the solution from the dispensing tube;

move the dispensing tube to another container;

move the magnet relative to the dispensing tube such that the effect of the magnetic field disappears and the magnetic beads are released from the side wall of the dispensing tube.

11. The device of claim 1, wherein the nucleic acid amplification module is configured for isothermal amplification or polymerase chain reaction (PCR).

12. The device of claim 1, wherein the nucleic acid amplification module further comprises a temperature regulator configured to independently heat or cool each of the plurality of chambers.

13. The device of claim 1, wherein the detection module is configured to detect labels carried by nucleic acids, and wherein the labels are identifiable by fluorescence, chemiluminescence, bioluminescence, radioluminescence, electroluminescence, electrochemiluminescence, mechanoluminescence, crystalline luminescence, thermoluminescence, sonoluminescence, phosphorescence, photoluminescence, enzymatic reactions, or radioactivity.

14. The device of claim 1, further comprising a liquid dispensing module to transfer or dispense samples or reagents in the device between two or more locations, the liquid dispensing module comprises: one or more sensors; one or more dispensing heads; and a Cartesian coordinate robot that provides 3-axis linear movement for the dispensing heads.

15. The device of claim 1, further comprising a reagent and consumable loading area comprising one or more of a pipette tip loading area, a PCR reagent storing and mixing processing area, and a waste area.

16. An in vitro diagnosis method, comprising using the device for extracting and detecting nucleic acids according to claim 1 to perform nucleic acid extraction and amplification on the sample.

17. The method of claim 16, wherein the diagnosis is for infection source identification, genetic disease, cancer detection, or genetic mutation detection.

18. An automated molecular in vitro diagnostic instrument, comprising the device for extracting and detecting nucleic acids of claim 1, and a computer-based automatic control system.

19. The diagnostic instrument of claim 18, wherein the diagnostic instrument is configured for infection source identification, genetic disease detection, cancer detection, or gene mutation detection.

20. The diagnostic instrument of claim 19, wherein the diagnostic instrument is configured for detection of a pathogen or a cancer, wherein the pathogen is selected from the group consisting of influenza virus, enterovirus, hepatitis B virus, hepatitis C virus, Ebola virus, Marburg virus, SARS virus, Zika virus, Bunya virus, rhinovirus, *Mycobacterium tuberculosis, Escherichia coli, Acinetobacter baumannii, Streptococcus pneumoniae, Streptococcus lactis, Urea sporococcus, Staphylococcus aureus, Bacillus subtilis, Bacillus anthracis, Streptococcus, Proteus, Vibrio cholerae*, and *Treponema pallidum*, or wherein the cancer is selected from the group consisting of gastric cancer, liver cancer, lung cancer, esophageal cancer, cervical cancer, breast cancer, colon cancer, rectal cancer, nasopharyngeal cancer, ovarian cancer, kidney cancer, bladder cancer, thyroid cancer, skin cancer, malignant tumors that grow from mesenchymal tissues including muscle, fat, bone, blood vessels, lymph, rhabdomyosarcoma, leiomyosarcoma, fibrosarcoma, liposarcoma, osteosarcoma, chondrosarcoma, angiosarcoma, lymphosarcoma, leukemia, Hodgkin's disease, Wilm's tumor (Wilms tumor), melanoma, retinocytoma, seminoma, granulosa cell tumor, Krukenberg tumor, Ewing's tumor, malignant hemangioendothelioma, and Paget's disease of the breast.

21. An in vitro diagnosis method, comprising using the diagnostic instrument according to claim 16 to perform nucleic acid extraction and amplification on the sample.

\*   \*   \*   \*   \*